United States Patent
Deecher et al.

(10) Patent No.: US 7,345,096 B2
(45) Date of Patent: Mar. 18, 2008

(54) USE OF NOREPINEPHRINE REUPTAKE MODULATORS FOR PREVENTING AND TREATING VASOMOTOR SYMPTOMS

(75) Inventors: Darlene Coleman Deecher, Quakertown, PA (US); Istvan Jozsef Merchenthaler, Chester Springs, PA (US); Liza Leventhal, Lawrenceville, NJ (US); Kimberly Jean Sipe, King of Prussia, PA (US); Lawrence Thomas O'Connor, Des Plaines, IL (US)

(73) Assignee: Wyeth, Madison, NJ (US)

( * ) Notice: Subject to any disclaimer, the term of this patent is extended or adjusted under 35 U.S.C. 154(b) by 589 days.

(21) Appl. No.: 10/684,777

(22) Filed: Oct. 14, 2003

(65) Prior Publication Data

US 2004/0143008 A1  Jul. 22, 2004

Related U.S. Application Data

(60) Provisional application No. 60/418,591, filed on Oct. 15, 2002.

(51) Int. Cl.
*A61K 31/12* (2006.01)
*A61K 31/16* (2006.01)
*A61K 31/045* (2006.01)
*A61K 31/275* (2006.01)

(52) U.S. Cl. ............... 514/675; 514/521; 514/626; 514/676; 514/683; 514/727

(58) Field of Classification Search ............ 514/675, 514/676, 683, 727
See application file for complete search history.

(56) References Cited

U.S. PATENT DOCUMENTS

| | | | |
|---|---|---|---|
| 3,454,554 A | 7/1969 | Biel et al. | 260/239 |
| 4,229,449 A | 10/1980 | Melloni et al. | 514/239.2 |
| 4,310,524 A | 1/1982 | Wiech et al. | 514/217 |
| 4,535,186 A | 8/1985 | Husbands et al. | 564/336 |
| 4,826,844 A | 5/1989 | Husbands et al. | 514/252 |
| 5,146,927 A * | 9/1992 | Czeisler et al. | 600/558 |
| 5,502,047 A | 3/1996 | Kavey | 514/183 |
| 2002/0107249 A1 | 8/2002 | Wong et al. | 514/238.5 |
| 2002/0128173 A1 | 9/2002 | Wong et al. | 514/1 |
| 2003/0036923 A1* | 2/2003 | Waldon et al. | 705/2 |
| 2003/0216366 A1* | 11/2003 | Leonard et al. | 514/182 |

FOREIGN PATENT DOCUMENTS

| | | |
|---|---|---|
| EP | 0 065 757 A1 | 12/1982 |
| EP | 0 303 961 A1 | 2/1989 |
| EP | 0 208 235 B1 | 1/1990 |
| EP | 1 266 659 A1 | 12/2002 |
| WO | 91/18602 A1 | 12/1991 |
| WO | WO98/36744 * | 8/1998 |
| WO | 99/44601 A1 | 9/1999 |
| WO | 02/064543 A1 | 8/2002 |
| WO | 03/037334 | 5/2003 |
| WO | 03/077897 A1 | 9/2003 |

OTHER PUBLICATIONS

Spence et al. Milnacipran A review of its use in depression. Drugs Sep. 1998: 56(3): pp. 405-427.*
Berendsen The role of serotonin in hot flushes. Maturitas 36 (2000) p. 155-164.*
Clinical Trial: "Phase III Randomized Study of Medroxyprogesterone Versus Venlafaxine in Women With Symptomatic Hot Flashes", www.clinicaltrials.gov sponsored by the National Institutes of Health, Study ID Numbers: CDR0000069217; NCCTG-N99C7; NCI-P02-0204, 2003, 6 pages.
Acs, N. et al., "Estrogen improves impaired musculocutaneous vascular adrenergic reactivity in pharmacologically ovariectomized rats: a potential peripheral mechanism for hot flashes?", *Endocrinology*, 2001 15: 68-73.
Barlow, D. H., "Venlafaxine for hot flushes," *Lancet*, Dec. 16, 2000, 356(9247): 2025-2026.
Barton, D. et al., "Hot Flashes—Aetiology and Management," *Drugs and Aging*, 2001, 18(8): 597-606.
Berendsen, H. H. G., "Hot Flushes and serotonin," *Journal of the British Menopause Society*, Mar. 2002, 8(1): 30-34.
Berendsen, H. H. G., "Effect of tibolone and raloxifene on the tail temperature of oestrogen-deficient rats," *European Journal of Pharmacology*, 2001, 419(1): 47-54.
Berendsen, H. H. G., "The role of serotonin in hot flushes," *Maturitas*, 2000, 36(3): 155-164.
Bundgaard, H., "Means to enhance penetration; Prodrugs as a means to improve the delivery of peptide drugs," *Advanced Drug Deliver Reviews*, 1992, 8, 1-38.
Bundgaard, H. et al., "Glycolamide Esters as Biolabile Prodrugs of Carboxylic Acid Agents: Synthesis, Stability, Bioconversion, and Physicochemical Properties," J. of Pharmaceutical Sciences, Apr. 1988, 77(4):285.
Casper, R. F. et al., "Neuroendocrinology of menopausal flushes: an hypothesis of flush mechanism," *Clinical Endocrinology*, 1985, 22: 293-312.
Fink, G. et al., "Oestrogen and mental state," *Nature*, 1996, 383(6598): 306.
Freedman, R. R. et al., "Clonidine raises the sweating threshold in symptomatic but not asymptomatic postmenopausal women," *Fertility & Sterility*, 2000, 74(1): 20-3.
Freedman, R. R., "Physiology of hot flashes," *American Journal of Human Biology*, 2001, 13: 453-464.
French, N., "$\alpha_2$-Adrenoceptors and $I_2$ sites in the mammalian central nervous system," *Pharmacol. Ther.*, 1995, 68(2):175-208.
Janowsky, et al., "Desipramine: an overview," *Journal of Clinical Psychiatry*, 1984, 45(10 Pt 2): 3-9.
Katovich, M. J. et al., "Mechanisms mediating the thermal response to morphine withdrawal in rats", *Proceedings of the Society for Experimental Biology& Medicine*, 1990, 193(2): 129-35.

(Continued)

*Primary Examiner*—Jennifer Kim
(74) *Attorney, Agent, or Firm*—Joseph E. Zahner

(57) ABSTRACT

The present invention relates to the use of compounds and composition of compounds that modulate norepinephrine levels for the prevention and treatment of vasomotor symptoms, such as hot flush, caused by, inter alia, thermoregulatory dysfunctions.

15 Claims, 6 Drawing Sheets

OTHER PUBLICATIONS

Katovich, M. J. et al., "Alpha-adrenergic mediation of the tail skin temperature response to naloxone in morphine-dependent rats," *Brain Research*, 1987, 426: 55-61.

Kramer et al., In: Murphy et al., *3rd Int'l Symposium on Recent Advances in Urological Cancer Diagnosis and Treatment-Proceedings*, Paris, France: SCI: 3-7 1992.

Krogsgaard-Larsen, et al., (ed). Design and Application of Prodrugs, Textbook of Drug Design and Development, Chapter 5, 113-191 1991.

Kronenberg et al., "Thermoregulatory Physiology of Menopausal Hot Flashes: A Review," *Can. J. Physiol. Pharmacol.*, 1987, 65:1312-1324.

Loprinzi, C.L. et al., "Venlafaxine in management of hot flashes in survivors of breast cancer: a randomized controlled trial," *Lancet*, Dec. 16, 2000, 356(9247): 2059-2063.

Loprinizi, C. L. et al. "Pilot Evaluation of Venlafaxine Hydrochloride for the Therapy of Hot Flashes in Cancer Survivors," *Journal of Clinical Oncology*, Jul. 1998, 16(7): 2377-2381.

Mackinnon et al., "$\alpha^2$-Adrenoceptors: more subtypes but fewer functional differences," *TIPS*, 1994, 15: 119-123.

Merchenthaler et al., "The effect of estrogens and antiestrogens in a rat model for hot flush," *Maturitas*, 1998, 30(3): 307-316.

Morin, S. M., "Atomoxetine Selectively Induces Fos Expression in the Rat Prefrontal Cortex," Presented at Society for Neuroscience Annual Meeting (SFN); Nov. 2-7, 2002, Orlando, FL.

Pacholczyk, T. et al., "Expression cloning of a cocaine-and antidepressant-sensitive human noradrenaline transporter," *Nature*, 1991, 350(6316): 350-4.

Panek, D.U. et al., "Effect of continuous intraventricular estrogen or catechol estrogen treatmetn on catecholamine turnover in various brain regions," *J. Pharmacol. Exp. Ther.*, 1986, 236(3), 646-652.

Prasad, P.D., et al., "Functional expression of the plasma membrane serotonin transporter but not the vesicular monoamine transporter in human placental trophoblasts and choriocarcinoma cells," Placenta, 1996, 17(4): 201-7.

Quella, S. K. et al., "Pilot evaluation of Venlafaxine for the treatment of hot flashes in men undergoing androgen ablation therapy for prostate cancer," *The Journal of Urology*, Jul. 1999, 162: 98-102.

Reneric, J-Ph. et al., "Idazoxan and 8-OH-DPAT modify the behavioral effects induced by either NA, or 5-HT, or dual NA/5-HT reuptake inhibition in the rat forced swimming test," *Nueropsychopharmacology*, Apr. 2001, 24(4): 379-390.

Rosenberg, J. et al., "Hypothesis: pathogenesis of postmenopausal hot flush," *Medical Hypotheses*, 1991, 35: 349-350.

Shaw, C. R., "The perimenopausal hot flash: epidemiology, physiology, and treatment," *Nurse Practitioner*, 1997, 22: 55-56, 61-66.

Stearns, V. et al., "Hot flushes," *Lancet*, Dec. 7, 2002, 360(9348): 1851-1861.

Stearns,V. et al., "Paroxetine controlled release in the treatment of menopausal hot flashes," *JAMA*, 2003, 289:2827-2834.

Stearns, V. et al., "A pilot trial assessing the efficacy of paroxetine hydrochloride (Paxil) in controlling hot flashes in breast cancer survivors," *Ann Oncol.*, 2000, 11:17-22.

Waldinger et al., "Treatment of hot flushes with mirtazapine: four case reports," *Maturitas*, 2000, 36(3): 165-168.

Wilen, S.H. *Tables of Resolving Agents and Optical Resolutions*, p. 268 E.L. Eliel, Ed., University of Notre Dame Press, Notre Dame, IN 1972.

Wilen, S.H., et al., "Strategies in optical resolutions," *Tetrahedron*, 33:2725, 1977.

Zhang, W. et al., "Synergistic Effects of Olanzapine and Other Antipsychotic Agents in Combination with Fluoxetine on Norepinephrine and Dopamine Release in Rat Prefrontal Cortex," *Neuropsychopharmacology*, 2000, 23(3): 250-262.

Eliel, E.L. *Stereochemistry of Carbon Compounds*, McGraw-Hill, NY, 1962.

*Remington's Pharmaceutical Sciences*, 17th edition, ed. Alfonoso R. Gennaro, Mack Publishing Company, Easton, PA 1985.

Bundgaard, (ed.), Design of Prodrugs, Elsevier 1985.

Widder, et al. (ed.), Methods in Enzymology, vol. 4, Academic Press 1985.

Jacques, et al., *Enantiomers, Racemates and Resolutions* Wiley Interscience, New York, 1981.

Higuchi and Stella (eds.) *Prodrugs as Novel Drug Delivery Systems*, American Chemical Society 1975.

U.S. Appl. No. 10/685,812, filed Oct. 14, 2003 Deecher et al.
U.S. Appl. No. 10/685,974, filed Oct. 14, 2003 Deecher et al.
U.S. Appl. No. 60/511,542, filed Oct. 14, 2003 Mahaney et al.
U.S. Appl. No. 60/511,042, filed Oct. 14, 2003 Mahaney et al.
U.S. Appl. No. 60/511,002, filed Oct. 14, 2003 Mahaney.
U.S. Appl. No. 60/510,811, filed Oct. 14, 2003 Trybulski et al.
U.S. Appl. No. 60/510,943, filed Oct. 14, 2003 Trybulski et al.
U.S. Appl. No. 60/511,001, filed Oct. 14, 2003 Mahaney et al.
U.S. Appl. No. 60/510,942, filed Oct. 14, 2003 Trybulski et al.

Spetz, A-C. E. et al., "Hot flushes in men: prevalence and possible mechanisms," *J. British Menopause Society*, Jun. 2002, 8(2), 57-62.

* cited by examiner

USE OF NOREPINEPHRINE REUPTAKE MODULATORS FOR PREVENTING AND TREATING VASOMOTOR SYMPTOMS

CROSS-REFERENCE TO RELATED APPLICATIONS

This application claims benefit of U.S. Application Ser. No. 60/418,591, filed Oct. 15, 2002, the disclosure of which is incorporated herein by reference in its entirety.

FIELD OF THE INVENTION

The present invention relates to the use of compounds and composition of compounds that modulate norepinephrine levels for the prevention and treatment of, inter alia, vasomotor symptoms (VMS).

BACKGROUND OF THE INVENTION

Vasomotor symptoms (VMS), referred to as hot flushes and night sweats, are the most common symptoms associated with menopause, occurring in 60% to 80% of all women following natural or surgically-induced menopause. VMS are likely to be an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women. It is well recognized that VMS are caused by fluctuations of sex steroid levels and can be disruptive and disabling in both males and females. A hot flush can last up to thirty minutes and vary in their frequency from several times a week to multiple occurrences per day. The patient experiences a hot flash as a sudden feeling of heat that spreads quickly from the face to the chest and back and then over the rest of the body. It is usually accompanied by outbreaks of profuse sweating. It may sometimes occur several times an hour, and it often occurs at night. Hot flushes and outbreaks of sweats occurring during the night can cause sleep deprivation. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., 3$^{rd}$ Int'l Symposium on Recent Advances in Urological Cancer Diagnosis and Treatment-Proceedings, Paris, France: SCI: 3-7 (1992)).

Hot flushes may be even more severe in women treated for breast cancer for several reasons: 1) many survivors of breast cancer are given tamoxifen, the most prevalent side effect of which is hot flush, 2) many women treated for breast cancer undergo premature menopause from chemotherapy, 3) women with a history of breast cancer have generally been denied estrogen therapy because of concerns about potential recurrence of breast cancer (Loprinzi, C. L., et al., Lancet, 2000, 356(9247): 2059-2063).

Men also experience hot flushes following steroid hormone (androgen) withdrawal. This is true in cases of age-associated androgen decline (Katovich, et al., Proceedings of the Society for Experimental Biology & Medicine, 1990, 193(2): 129-35) as well as in extreme cases of hormone deprivation associated with treatments for prostate cancer (Berendsen, et al., European Journal of Pharmacology, 2001, 419(1): 47-54. As many as one-third of these patients will experience persistent and frequent symptoms severe enough to cause significant discomfort and inconvenience.

The precise mechanism of these symptoms is unknown but generally is thought to represent disturbances to normal homeostatic mechanisms controlling thermoregulation and vasomotor activity (Kronenberg et al., "Thermoregulatory Physiology of Menopausal Hot Flashes: A Review," Can. J. Physiol. Pharmacol., 1987, 65:1312-1324).

The fact that estrogen treatment (e.g. estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (J. Pharmacology & Experimental Therapeutics, 1986, 236(3) 646-652). It is hypothesized that estrogens modulate NE and 5-HT levels providing homeostasis in the thermoregulatory center of the hypothalamus. The descending pathways from the hypothalamus via brainstem/spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al. Lancet, 2000, 356:2059-2063; Stearns et al., JAMA, 2003, 289:2827-2834) compared to doses used to treat the behavioral aspects of depression. The interplay of the CNS/PNS in the pathophysiology of VMS and the presented data within this document were used to support the claims that the norepinephrine system could be targeted to treat VMS.

Although VMS are most commonly treated by hormone therapy (orally, transdermally, or via an implant), some patients cannot tolerate estrogen treatment (Berendsen, Maturitas, 2000, 36(3): 155-164, Fink et al., Nature, 1996, 383(6598): 306). In addition, hormone replacement therapy is usually not recommended for women or men with or at risk for hormonally sensitive cancers (e.g. breast or prostate cancer). Thus, non-hormonal therapies (e.g. fluoxetine, paroxetine [SRIs] and clonidine) are being evaluated clinically. WO9944601 discloses a method for decreasing hot flushes in a human female by administering fluoxetine. Other options have been studied for the treatment of hot flashes, including steroids, alpha-adrenergic agonists, and beta-blockers, with varying degree of success (Waldinger et al., Maturitas, 2000, 36(3): 165-168).

It has been reported that $\alpha_2$-adrenergic receptors play a role in thermoregulatory dysfunctions (Freedman et al., Fertility & Sterility, 2000, 74(1): 20-3). These receptors are located both pre and post synaptically and mediate an inhibitory role in the central and peripheral nervous system. There are four distinct subtypes of the adrenergic$_{\alpha 2}$ receptors, i.e., are $\alpha_{2A}$, $\alpha_{2B}$, $\alpha_{2C}$ and $\alpha_{2D}$ (Mackinnon et al., TIPS, 1994, 15: 119; French, Pharmacol. Ther., 1995, 68: 175). It has been reported that a non-select $\alpha_2$-adrenoceptor antagonist, yohimbine, induces a flush and an $\alpha_2$-adrenergic receptor agonist, clonidine, alleviates the yohimbine effect (Katovich, et al., Proceedings of the Society for Experimental Biology & Medicine, 1990, 193(2): 129-35, Freedman et al., Fertility & Sterility, 2000, 74(1): 20-3). Clonidine has been used to treat hot flush. However, using such treatment is associated with a number of undesired side effects caused by high doses necessary to abate hot flash described herein and known in the related arts.

Given the complex multifaceted nature of thermoregulation and the interplay between the CNS and PNS in maintaining thermoregulatory homeostasis, multiple therapies and approaches can be developed to target vasomotor symptoms. The present invention focuses on novel methods of recovery of activity of NE by modulating the noradrenergic system.

SUMMARY OF THE INVENTION

The invention is directed to compounds and compositions containing compounds to modulate norepinephrine levels for the prevention and treatment of, inter alia, vasomotor symptoms (VMS) caused by, for example, thermoregulatory dysfunctions, such as those experienced by pre-, peri- and post menopausal females and naturally, chemically or surgically andropausal males. In some aspects, the present invention relates to the use of compounds and compositions of norepinephrine reuptake inhibitors alone or in combination with serotonin reuptake inhibitors for the modulation of the norepinephrine system. In other aspects, the present invention relates to the use of compounds and composition of compounds having norepinephrine reuptake inhibitor activity in combination with adrenergic$_{\alpha 2}$ receptor antagonist activity, as either a single compound or a combination of compounds. In yet other embodiments, the invention relates to the use of compounds and composition of compounds having dual NRI/SRI activity.

In one embodiment, the present invention is directed to methods for treating or preventing vasomotor symptoms in a subject in need thereof, comprising the step of:

administering to said subject a composition, comprising a therapeutically effective amount of at least one norepinephrine reuptake inhibitor or pharmaceutically acceptable salt thereof.

In preferred embodiments, the compound has a selectivity ratio of SERT:NET of less than about 1,000:1. In other preferred embodiments, the compound has a selectivity ratio of SERT:NET of greater than about 2:1, more preferably, greater than about 5:1, and even more preferably, greater than about 10:1.

In other preferred embodiments, the invention is directed to methods wherein the composition further comprises a therapeutically effective amount of at least one serotonin reuptake inhibitor or a pharmaceutically acceptable salt thereof. In certain preferred embodiments, the norepinephrine reuptake inhibitor and the serotonin reuptake inhibitor are administered concurrently.

In yet other preferred embodiments, the invention is directed to methods wherein the composition further comprises a therapeutically effective amount of at least one adrenergic$_{\alpha 2}$ receptor antagonist or a pharmaceutically acceptable salt thereof. In certain preferred embodiments, the norepinephrine reuptake inhibitor and the adrenergic$_{\alpha 2}$ receptor antagonist are administered simultaneously or concurrently. In certain preferred embodiments, the adrenergic$_{\alpha 2}$ receptor antagonist is selective for the adrenergic$_{\alpha 2A}$ receptor, adrenergic$_{\alpha 2B}$ receptor, adrenergic$_{\alpha 2C}$ receptor, or adrenergic$_{\alpha 2D}$ receptor.

In yet other embodiments, the invention is directed to methods for treating or preventing vasomotor symptoms in a subject in need thereof, comprising the step of:

administering to said subject a therapeutically effective amount of at least one dual NRI/SRI compound or pharmaceutically acceptable salt thereof, wherein said amount is less than about 37.5 mg/day.

In other embodiments, the invention is directed to pharmaceutical compositions, comprising:

a. at least one norepinephrine reuptake inhibitor or a pharmaceutically acceptable salt thereof;
b. at least one serotonin reuptake inhibitor or a pharmaceutically acceptable salt thereof; and
c. at least one pharmaceutically acceptable carrier.

In other embodiments, the invention is directed to pharmaceutical compositions, comprising:

a. at least one norepinephrine reuptake inhibitor or a pharmaceutically acceptable salt thereof;
b. at least one adrenergic$_{\alpha}$2 receptor antagonist or a pharmaceutically acceptable salt thereof; and
c. at least one pharmaceutically acceptable carrier.

In certain preferred embodiments, the norepinephrine reuptake inhibitor and adrenergic$_{\alpha}$2 receptor antagonist are a single compound. In other preferred embodiments, norepinephrine reuptake inhibitor and adrenergic$_{\alpha}$2 receptor antagonist are a combination of two or more compounds.

BRIEF DESCRIPTION OF THE DRAWINGS

The invention can be more fully understood from the following detailed description and the accompanying drawings that form a part of this application.

FIG. 3A shows a dose response in morphine-dependent rat model of hot flush (MD model) for desipramine. FIG. 3B shows desipramine 10 mg/kg, sc in OVX-induced thermoregulatory dysfunction telemetry model (telemetry model). FIG. 3C shows reboxetine dose response in MD model. FIG. 3D shows changes in TST over time in MD model for reboxetine at various doses. FIG. 3E shows changes in TST over time in MD model for 1-[1-(3-chlorophenyl)-2-(4-methyl-1-piperazinyl)ethyl]cyclohexanol (824) at various doses. FIG. 3F shows maximal flush for vehicle, 1-[1-(3-chlorophenyl)-2-(dimethylamino)ethyl] cyclohexanol (WY-781), and 1-[2-(dimethylamino)-1-(3-trifluoromethylphenyl)ethyl]cyclohexanol (WY-867).

DETAILED DESCRIPTION OF THE INVENTION

The invention is directed to compounds and compositions containing compounds to modulate norepinephrine levels for the prevention and treatment of, inter alia, vasomotor symptoms (VMS) caused by, for example, thermoregulatory dysfunctions, such as those experienced by pre-, peri- and post menopausal females and naturally, chemically or surgically andropausal males. In some aspects, the present invention relates to the use of compounds and compositions of norepinephrine reuptake inhibitors alone or in combination with serotonin reuptake inhibitors for the modulation of the norepinephrine system. In other aspects, the present invention relates to the use of compounds and composition of compounds having norepinephrine reuptake inhibitor activity in combination with adrenergic$_{\alpha 2}$ receptor antagonist activity, either as a single compound or a combination of compounds.

It is believed that the present invention described presents a substantial breakthrough in the field of treatment, alleviation, inhibition, and/or prevention of vasomotor instability and/or dysfunction.

Figure 1:
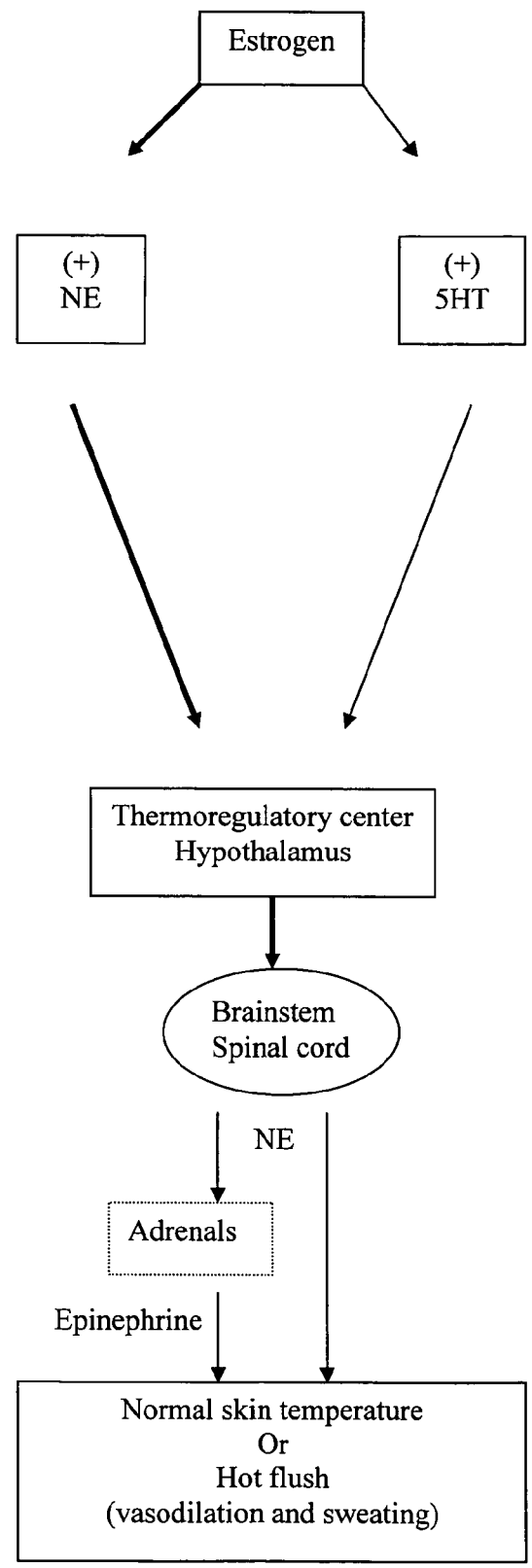
FIG. 1 is an overview of estrogen action on norepinephrine/serotonin mediated thermoregulation.

When estrogen levels are low or estrogen is absent, the normal levels between NE and 5-HT is altered and this altered change in neurotransmitter levels may result in changes in the sensitivity of the thermoregulatory center. The altered chemical levels may be translated in the thermoregulatory center as heat sensation and as a response, the hypothalamus may activate the descending autonomic pathways and result in heat dissipation via vasodilation and sweating (hot flush) (FIG. 1). Accordingly, the estrogen deprivation may result in altered norepinephrine activity.

Figure 2:
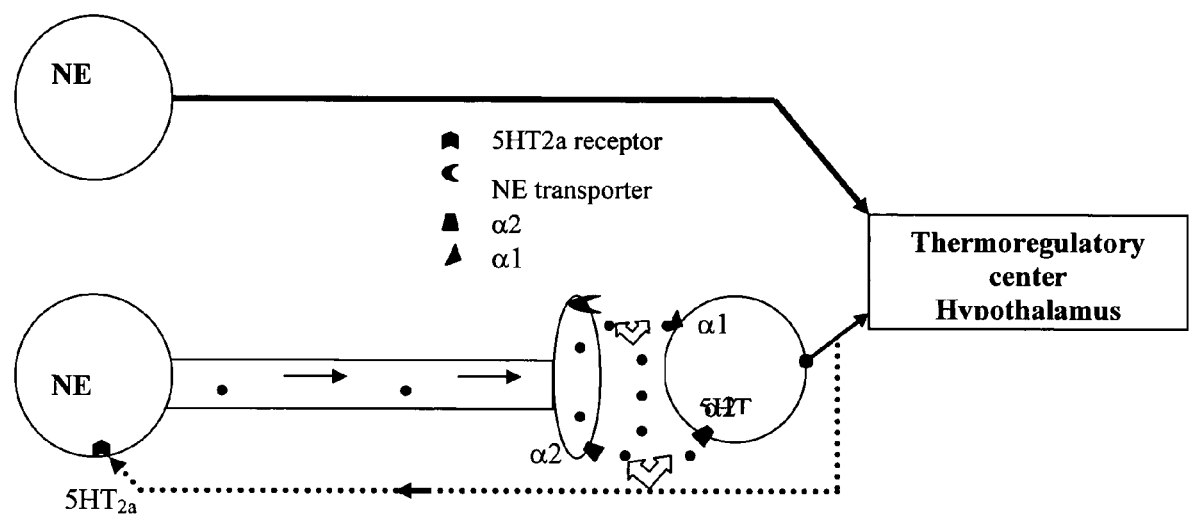
FIG. 2 is a schematic representation of the interactions of norepinephrine and serotonin and their respective receptors (5-HT$_{2a}$, $\alpha_1$ and $\alpha_2$-adrenergic).

Norepinephrine synthesized in perikarya of the brainstem is released at the nerve terminals in the hypothalamus and brainstem. In the hypothalamus, NE regulates the activity of neurons residing in the thermoregulatory center. In the brainstem, NE innervates serotoninergic neurons (5HT), and acting via adrenergic$_{\alpha 1}$ and adrenergic$_{\alpha 2}$ postsynaptic receptors, it stimulates the activity of the serotoninergic system. In response, 5-HT neurons also modulate the activity the thermoregulatory center and feedback to NE neurons. Via this feedback connection, 5-HT, acting via 5-HT$_{2a}$ receptors, inhibit the activity of NE neurons. Norepinephrine in the synaptic cleft is also taken up by NE transporter (NET) located in NE neurons. The transporter recycles NE and makes it available for multiple neurotransmission (FIG. 2).

The present invention provides a treatment for vasomotor symptoms by methods of recovering the reduced activity of norepinephrine. Norepinephrine activity in the hypothalamus or in the brainstem can be elevated by (i) blocking the activity of the NE transporter, (ii) blocking the activity of the presynaptic adrenergic $_{\alpha 2}$ receptor with an antagonist, or (iii) blocking the activity of 5-HT on NE neurons with a 5-HT$_{2a}$ antagonist.

In one embodiment, it was discovered that using NRI compounds at low doses, below doses commonly used for antidepressant efficacy, results in an improved treatment to maintain normal thermoregulatory homeostasis. Furthermore, NRI compounds in combination with SRI compounds surprisingly results in such benefits as clearer dose-related definitions of efficacy, diminished reported side effect, superior therapy due to synergistic activity, and accordingly, an improved therapeutic index. For example, high doses of NRIs or NRI/SRI compounds alone can induce vomiting, nausea, sweating, and flushes (Janowsky, et al., *Journal of Clinical Psychiatry*, 1984, 45(10 Pt 2): 3-9). The present invention provides treatment or prevention of vasomotor symptoms without side effects caused by using NRI alone at high doses.

In one embodiment, the present invention is directed to methods for treating or preventing vasomotor symptoms in a subject in need thereof, comprising the step of:

administering to said subject a composition, comprising a therapeutically effective amount of at least one norepinephrine reuptake inhibitor or pharmaceutically acceptable salt thereof.

In preferred embodiments, the compound has a selectivity ratio of SERT:NET of less than about 1,000:1. In other preferred embodiments, the compound has a selectivity ratio of SERT:NET of greater than about 2:1, more preferably, greater than about 5:1, and even more preferably, greater than about 10:1.

In other preferred embodiments, the invention is directed to methods wherein the composition further comprises a therapeutically effective amount of at least one serotonin reuptake inhibitor or a pharmaceutically acceptable salt thereof. In certain preferred embodiments, the norepinephrine reuptake inhibitor and the serotonin reuptake inhibitor are administered concurrently. A low dose of a known NRI compound, desipramine was able to reduce the TST by 50% compared to vehicle treated rats in a naloxone-induced hot flush.

Examples of SRIs include, but are not limited to, fluoxetine, paroxetine, sertraline, fluvoxamine, and combinations and pharmaceutically acceptable salts thereof.

Examples of NRIs include, but are not limited to, maprotiline; reboxetine; norpramine/desipramine; nisoxetine; atomoxetine; amoxapine; doxepin; lofepramin; amitryptyline; 1-[1-(3-fluorophenyl)-2-(4-methyl-1-piperazinyl)ethyl]cyclohexanol; 1-[1-(3-chlorophenyl)-2-(4-methyl-1-piperazinyl)ethyl]cyclohexanol; 1-[2-(4-methyl-1-piperazinyl)-1-[3-(trifluoromethyl)-phenyl]ethyl]cyclohexanol; 1-[1-(4-methoxyphenyl)-2-[4-methyl-1-piperazinyl)ethyl] cyclohexanol; 1-[1-(3-chlorophenyl)-2-[4-(3-chlorophenyl)-1-piperazinyl]ethyl]cyclohexanol; 1-[1-(3-methoxyphenyl)-2-[4-phenyl methyl)-1-piperazinyl]ethyl] cyclohexanol; 1-[2-(3-chlorophenyl)-1-piperazinyl]-1-[3-methoxyphenyl)ethyl]cyclohexanol; 1-[2-[4-(6-chloro-2-pyrazinyl)-1-piperazinyl]-1-[3-methoxyphenyl)ethyl] cyclohexanol; 1-[2-[4-(phenyl methyl)]-1-piperazinyl]-1-[3-(trifluoromethyl)phenyl]ethyl]cyclohexanol; 1-[1-(3-methoxyphenyl)-2-[4-[3-(trifluoro methyl)-phenyl]-1-piperazinyl]ethyl]cyclohexanol; 1-[1-(4-fluorophenyl)-2-[4-(phenylmethyl)-1-piperazinyl]ethyl]cyclohexanol; 1-[1-(3-methoxyphenyl)-2-[4-[3-(trifluoromethyl)-phenyl]-1-piperazinyl]ethyl]cyclopentanol; 1[1-(4-fluorophenyl)-2-[4-(phenylmethyl)-1-piperazinyl]ethyl]cyclohexanol; 1-[2-(dimethylamino)-1-(3-trifluoromethylphenyl)ethyl] cyclohexanol; 1-[1-(3-fluorophenyl)-2-(4-methyl-1-piperazinyl)ethyl]cyclohexanol; 1-[1-(3-chlorophenyl)-2-(dimethylamino)ethyl]cyclohexanol; 1-[2-dimethylamino)-1-(3-trifluoromethylphenyl)ethyl]cyclohexanol; 1-[1-(3-chlorophenyl)-2-piperazin-1-yl-ethyl]-cyclohexanol; and combinations and pharmaceutically acceptable salts thereof. Preferred NRIs include is desipramine and 1-[1-(3-chlorophenyl)-2-(4-methyl-1-piperazinyl)ethyl]cyclohexanol, particularly pure R and S enantiomers of 1-[1-(3-chlorophenyl)-2-(4-methyl-1-piperazinyl)ethyl]cyclohexanol. The dimethyl amine derivatives may be synthesized as described, for example, in U.S. Pat. No. 4,535,186, the disclosure of which is incorporated herein by reference in its entirety. The piperazine derivatives may be synthesized as described, for example, in U.S. Pat. No. 4,826,844, the disclosure of which is incorporated herein by reference in its entirety.

In another embodiment, a dual acting compound with norepinephrine reuptake inhibitor (NRI) activity and serotonin reuptake inhibitor (SRI) activity plays an important role in maintaining normal body temperature. A SRI compound alone did not abate hot flush. Surprisingly, an NRI compound, desipramine, when co-administered with a SRI compound resulted in significantly enhanced abatement of naloxone-induced hot flush. Accordingly, the efficacy of norepinephrine reuptake inhibitor was significantly increased in the presence of serotonin reuptake inhibitor.

In yet another embodiments, the invention is directed to methods for treating or preventing vasomotor symptoms in a subject in need thereof, comprising the step of:
  administering to said subject a therapeutically effective amount of at least one dual NRI/SRI compound or pharmaceutically acceptable salt thereof,
  wherein said amount is less than about 37.5 mg/day, preferably, less than about 30 mg/day, even more preferably, less than about 25 mg/day, yet even more preferably, less than about 20 mg/day, less than about 15 mg/day, less than about 10 mg/day, and less than about 5 mg/day. Surprisingly, these therapeutically effective amounts are lower than levels used in the prior art to achieve abatement of vasomotor symptoms.

Examples of dual NRI/SRI compounds are venlafaxine, O-desmethyl-venlafaxine (DVS-233 or ODV), milnacipran, duloxetine, and combinations and pharmaceutically acceptable salts thereof. Accordingly, any combination of the above mentioned NRI or SRI such as venlafaxine, duloxetine, or milnacipran or components that have dual NRI/SRI activity (dual acting compound) could be used to maintain normal thermoregulatory homeostasis without reported side effects.

In yet another embodiment, venlafaxine was able to alleviate an elevated naloxone-dependent hot flush induced by an adrenergic$_{\alpha 2}$ receptor antagonist, atipamezole. The results indicated a possible mechanism for venlafaxine increasing norepinephrine signaling through the adrenergic$_{\alpha 2}$ receptor.

Figure 4:
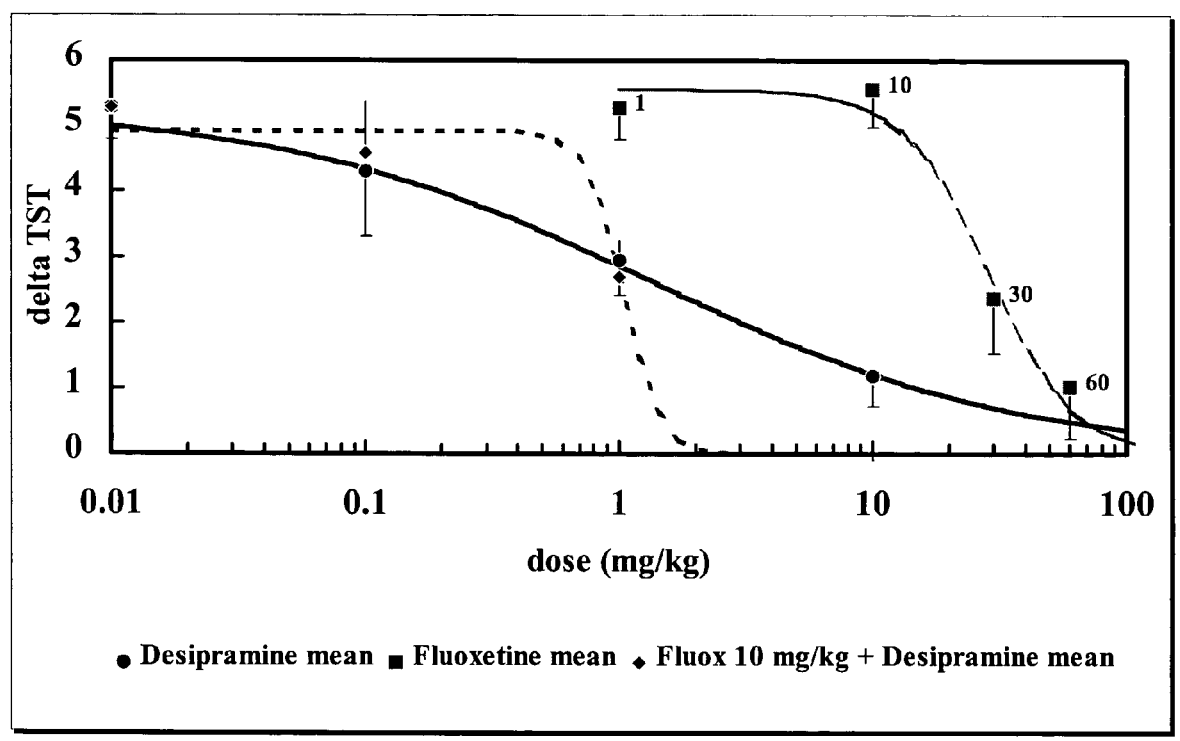
FIG. 4 shows NRI (desipramine) dose response in combination with SRI (fluoxetine 10 mg/kg) in morphine-dependent rat model of hot flush (referred to in Example 2).

The combination of an NRI and an SRI has several additional advantages over the use of SRI alone to treat vasomotor symptoms. SRI alone induces vomiting, nausea and sexual dysfunction (*Annals of Oncology*, 2000, 11:17-22). The combination of SRI and NRI activity will reduce the effective dose of SRI and will result in reduction of SRI side effects along with faster onset of the drug action. For example, when an increasing dose of NRI and a 10 mg/kg dose of SRI were co-administered, hot flush was abated by 100% at a 3 mg/kg dose of desipramine (FIG. 4) compared with the 10 mg/kg dose.

In yet other preferred embodiments, the invention is directed to methods wherein the composition further comprises a therapeutically effective amount of at least one adrenergic$_{\alpha 2}$ receptor antagonist or a pharmaceutically acceptable salt thereof. In certain preferred embodiments, the norepinephrine reuptake inhibitor and the adrenergic$_{\alpha 2}$ receptor antagonist are administered simultaneously or concurrently. In certain preferred embodiments, the adrenergic$_{\alpha 2}$ receptor antagonist is selective for the adrenergic$_{\alpha 2A}$ receptor, adrenergic$_{\alpha 2B}$ receptor, adrenergic$_{\alpha 2C}$ receptor, or adrenergic$_{\alpha 2D}$ receptor.

Adrenergic$_{\alpha 2}$ receptor antagonists are known to induce hot flush. Surprisingly, an adrenergic$_{\alpha 2}$ receptor antagonist when co-administered with a NRI compound, resulted in hot flush abatement. In one embodiment, the abatement of a naloxone-induced flush was enhanced by more than 50% when a NRI was co-administered with an adrenergic$_{\alpha 2}$ receptor antagonist. Thus, demonstrating that the efficacy of an NRI was potentiated when administered in combination with an adrenergic$_{\alpha 2}$ receptor antagonist. The dose level may require adjustment according to the dose of adrenergic$_{\alpha 2}$ receptor antagonist administered, in order to block side effects without altering the efficacy on hot flushes. One of ordinary skill in the art will know how to determine such doses without undue experimentation.

Examples of adrenergic$_{\alpha 2}$ receptor antagonist include, but are not limited to, atipamezole; 2-[2-(4-(2-methoxyphenyl)piperazin-1-yl)ethyl]-4,4-dimethyl-1,3-(2H,4H)-isoquinolindione dihydrochloride (ARC 239 dihydrochloride); 2-[(4,5-dihydro-1H-imidazol-2-yl)methyl]-2,3-dihydro-1-methyl-1H-isoindole maleate (BRL 44408 maleate); BRL48962; BRL41992; SKF 104856; SKF 104078; MK912; 2-(2-ethyl-2,3-dihydro-2-benzofuranyl)-4,5-dihydro-1H-imidazole hydrochloride (efaroxan hydrochloride); 2-(1,4-benzodioxan-2-yl)-2-imidazoline hydrochloride (idazoxan hydrochloride); 2-(1-ethyl-2-indazoyl)methyl-1,4-benzodioxan hydrochloride (imiloxan hydrochloride); 17α-hydroxy-20α-yohimban-16β-carboxylic acid, methyl ester hydrochloride (rauwolscine hydrochloride); (8αR,12αS,13αS)-5,8,8α,9,10,11,12,12α,13,13α-dechydro-3-methoxy-12-(ethylsulfonyl)-6H-isoquino[2,1-γ][1,6]naphthyridine hydrochloride (RS 79948 hydrochloride); 2-(2,3-dihydro-2-methoxy-1,4-benzodioxin-2-yl)-4,5-dihydro-1H-imidazole hydrochloride (RX 821002 hydrochloride); 8-[(2,3-dihydro-1,4-benzodioxin-2-yl)methyl]-1-phenyl-1,3,8-triazaspiro[4,5]decan-4-one (spiroxatrine); 17α-hydroxyyohimban-16α-carboxylic acid methyl ester hydrochloride (yohimbine hydrochloride); and combinations and pharmaceutically acceptable salts thereof. Several of these compounds are available from Tocris Cookson Inc., Ellisville, Mo.

In certain preferred embodiments, the adrenergic$_{\alpha 2}$ receptor antagonist is selective for the adrenergic$_{\alpha 2A}$ receptor, adrenergic$_{\alpha 2B}$ receptor, adrenergic$_{\alpha 2C}$ receptor, or adrenergic$_{\alpha 2D}$ receptor. BRL44408 and BRL48962 are known to be selective adrenergic$_{\alpha 2A}$ receptor antagonists. Imiloxan is a known selective adrenergic$_{\alpha 2A}$ receptor antagonist. Rauwolscine and MK912 are known selective adrenergic$_{\alpha 2A}$ receptor antagonists.

In other embodiments, the invention is directed to pharmaceutical compositions, comprising:
a. at least one norepinephrine reuptake inhibitor or a pharmaceutically acceptable salt thereof;
b. at least one serotonin reuptake inhibitor or a pharmaceutically acceptable salt thereof; and
c. at least one pharmaceutically acceptable carrier.

Generally, the norepinephrine reuptake inhibitor or a pharmaceutically acceptable salt thereof will be present at a level of from about 0.1%, by weight, to about 90% by weight, based on the total weight of the pharmaceutical composition, and serotonin reuptake inhibitor or a pharmaceutically acceptable salt thereof will be present at a level of from about 0.1%, by weight, to about 90% by weight, based on the total weight of the pharmaceutical composition. Preferably, the norepinephrine reuptake inhibitor or a pharmaceutically acceptable salt thereof will be present at a level of at least about 1%, by weight, and the serotonin reuptake inhibitor will be present at a level of at least about 1%, based on the total weight of the pharmaceutical composition. More preferably, the norepinephrine reuptake inhibitor or a pharmaceutically acceptable salt thereof will be present at a level of at least about 5%, by weight, and the serotonin reuptake inhibitor will be present at a level of at least about 5%, based on the total weight of the pharmaceutical composition. Even more preferably, the norepinephrine reuptake inhibitor or a pharmaceutically acceptable salt thereof will be present at a level of at least about 10%, by weight, and the serotonin reuptake inhibitor will be present at a level of at least about 10%, based on the total weight of the pharmaceutical composition. Yet even more preferably, the norepinephrine reuptake inhibitor or a pharmaceutically acceptable salt thereof will be present at a level of at least about 25%, by weight, and the serotonin reuptake inhibitor will be present at a level of at least about 25%, based on the total weight of the pharmaceutical composition.

In other embodiments, the invention is directed to pharmaceutical compositions, comprising:
a. at least one norepinephrine reuptake inhibitor or a pharmaceutically acceptable salt thereof;
b. at least one adrenergic$_\alpha$2 receptor antagonist or a pharmaceutically acceptable salt thereof; and
c. at least one pharmaceutically acceptable carrier.

Generally, the norepinephrine reuptake inhibitor or a pharmaceutically acceptable salt thereof will be present at a level of from about 0.1%, by weight, to about 90% by weight, based on the total weight of the pharmaceutical composition, and adrenergic$_\alpha$2 receptor antagonist or a pharmaceutically acceptable salt thereof will be present at a level of from about 0.1%, by weight, to about 90% by weight, based on the total weight of the pharmaceutical composition. Preferably, the norepinephrine reuptake inhibitor or a pharmaceutically acceptable salt thereof will be present at a level of at least about 1%, by weight, and the adrenergic$_\alpha$2 receptor antagonist will be present at a level of at least about 1%, based on the total weight of the pharmaceutical composition. More preferably, the norepinephrine reuptake inhibitor or a pharmaceutically acceptable salt thereof will be present at a level of at least about 5%, by weight, and the adrenergic$_\alpha$2 receptor antagonist will be present at a level of at least about 5%, based on the total weight of the pharmaceutical composition. Even more preferably, the norepinephrine reuptake inhibitor or a pharmaceutically acceptable salt thereof will be present at a level of at least about 10%, by weight, and the adrenergic$_\alpha$2 receptor antagonist will be present at a level of at least about 10%, based on the total weight of the pharmaceutical composition. Yet even more preferably, the norepinephrine reuptake inhibitor or a pharmaceutically acceptable salt thereof will be present at a level of at least about 25%, by weight, and the adrenergic$_\alpha$2 receptor antagonist will be present at a level of at least about 25%, based on the total weight of the pharmaceutical composition.

In certain preferred embodiments, the norepinephrine reuptake inhibitor and adrenergic$_\alpha$2 receptor antagonist are a single compound. In other preferred embodiments, norepinephrine reuptake inhibitor and adrenergic$_\alpha$2 receptor antagonist are a combination of two or more compounds.

Such compositions are prepared in accordance with acceptable pharmaceutical procedures, such as described in *Remingtons Pharmaceutical Sciences,* 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The phrases "vasomotor symptoms," "vasomotor instability symptoms" and "vasomotor disturbances" include, but are not limited to, hot flushes (flashes), insomnia, sleep disturbances, mood disorders, irritability, excessive perspiration, night sweats, fatigue, and the like, caused by, inter alia, thermoregulatory dysfunction.

The term "hot flush" is an art-recognized term that refers to an episodic disturbance in body temperature typically consisting of a sudden skin flushing, usually accompanied by perspiration in a subject. The term "hot flush" may be used interchangeably with the terms vasomotor symptoms, vasomotor instability, vasomotor dysfunction, night sweats, vasomotor disturbances, and hot flash.

The phrase "a compound having norepinephrine reuptake inhibitor activity," as used herein, refers to a compound that alters the level of norepinephrine (NE) by inhibiting the uptake of NE through neurons of the central and/or peripheral nervous system and/or the peripheral system and that has a selectivity ratio of SERT:NET activity, as measured by the $EC_{50}$ value or by % specific bound NE uptake for the human transporter, of at least about 1:1. Preferably, the selectivity ratio of SERT:NET does not exceed about 1000:1. Preferably, the selectivity ratio of SERT:NET is greater than about 2:1. More preferably, the selectivity ratio of SERT:NET is greater than about 5:1. Even more preferably, the selectivity ratio of SERT:NET is greater than about 10:1.

The phrase "a compound having serotonin reuptake inhibitor activity," as used herein, refers to a compound that increases the level of serotonin by inhibiting the uptake of serotonin through neurons of the central and/or peripheral nervous system and/or the peripheral system.

The phrase "a compound having dual NRI/SRI activity," as used herein, refers to a single compound having dual activity as a serotonin reuptake inhibitor and as a norepinephrine reuptake inhibitor. As used herein, a compound having a dual activity is a dual acting compound.

The abbreviations in the specification correspond to units of measure, techniques, properties, or compounds as follows: "min" means minutes, "h" means hour(s), "μL" means microliter(s), "mL" means milliliter(s), "mM" means millimolar, "M" means molar, "mmole" means millimole(s), "cm" means centimeters, "SEM" means standard error of the mean and "IU" means International Units. "$\Delta°$ C." and $\Delta$ TST mean change in tail skin temperature normalized for 15 minutes baseline TST prior to naloxone-induced flush. "$ED_{50}$ value" means dose which results in 50% alleviation of the observed condition or effect (50% mean maximum endpoint).

"Tail skin temperature" is abbreviated TST.
"Norepinephrine transporter" is abbreviated NET.
"Human norepinephrine transporter" is abbreviated hNET.
"Serotonin transporter" is abbreviated SERT.
"Human serotonin transporter" is abbreviated hSERT.
"Norepinephrine reuptake inhibitor" is abbreviated NRI.
"Selective norepinephrine reuptake inhibitor" is abbreviated SNRI.
"Serotonin reuptake inhibitor" is abbreviated SRI.
"Selective serotonin reuptake inhibitor" is abbreviated SSRI.
"Norepinephrine" is abbreviated NE.
"Serotonin is abbreviated 5-HT.
"Subcutaneous" is abbreviated sc.
"Intraperitoneal" is abbreviated ip.
"Oral" is abbreviated po.

In the context of this disclosure, a number of terms shall be utilized. The term "treatment" as used herein includes preventative (e.g., prophylactic), curative or palliative treatment and "treating" as used herein also includes preventative, curative and palliative treatment.

A "therapeutically effective amount" refers to an amount effective, at dosages, and for periods of time necessary, to achieve the desired result. In particular, "therapeutically effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

It will be appreciated that the therapeutically effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the components are outweighed by the therapeutically beneficial effects.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment.

For example, for a patient who experiences any number of hot flushes, compounds having NRI activity or combination of compounds SRI and NRI activities may be administered, preferably, at a dosage of from about 0.1 mg/day to about 200 mg/day, more preferably from about 1 mg/day to about 100 mg/day and most preferably from about 1 mg/day to 50 mg/day for a time sufficient to reduce and/or substantially eliminate the number and/or severity of hot flushes or such that hot flushes.

Furthermore, a compound having an NRI activity can be co-administered with a compound having adrenergic$_{\alpha 2}$ receptor antagonist activity preferably at dosage of about 0.1 mg/day to about 300 mg/day, more preferably from about 1 mg/day to 200 mg/day, and most preferably from about 1 mg/day to 100 mg/day for a time sufficient to reduce and/or substantially eliminate the number and/or severity of hot flushes or such that hot flushes.

The terms "component," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action. The component herein may contain NRI activity alone or combination of NRI and SRI activity. The component of the present invention may contain substantially no SRI activity or exhibit NRI activity essentially in the absence of SRI activity. Furthermore, the compound of the present invention may contain combination of NRI activity and in combination with adrenergic$_{\alpha 2}$ receptor antagonist activity.

The terms "component", "drug" or "pharmacologically active agent" or "active agent" or "medicament" are used interchangeably herein to refer to a compound or compounds or composition of matter which, when administered to an organism (human or animal) induces a desired pharmacologic and/or physiologic effect by local and/or systemic action. The component herein may contain norepinephrine reuptake inhibiting activity or combined serotonin reuptake inhibiting activity and the norepinephrine reuptake inhibiting activity. Furthermore, the component herein may contain combined norepinephrine reuptake inhibiting activity and the adrenergic $_{\alpha 2}$ receptor antagonist activity.

The term "modulation" refers to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

As used herein, the term "inhibitor" refers to any agent that inhibits, suppresses, represses, or decreases a specific activity, such as serotonin reuptake activity or the norepinephrine reuptake activity.

The term "inhibitor" is intended to comprise any compound, e.g., antibody, small molecule, peptide, oligopeptide, polypeptide, or protein, preferably small molecule or peptide, that exhibits a partial, complete, competitive and/or inhibitory effect on mammalian, preferably the human norepinephrine reuptake or both serotonin reuptake and the norepinephrine reuptake, thus diminishing or blocking, preferably diminishing, some or all of the biological effects of endogenous norepinephrine reuptake or of both serotonin reuptake and the norepinephrine reuptake.

Within the present invention, the NRIs, SRIs, NRI/SRIs, and adrenergic$_{\alpha 2}$ receptor antagonists may be prepared in the form of pharmaceutically acceptable salts. As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferably is the hydrochloride salt.

"Administering," as used herein, means either directly administering a compound or composition of the present invention, or administering a prodrug, derivative or analog which will form an equivalent amount of the active compound or substance within the body.

The present invention includes prodrugs of NRIs, SRIs, NRI/SRIs, and adrenergic$_{\alpha 2}$ receptor antagonists. "Prodrug," as used herein, means a compound which is convertible in vivo by metabolic means (e.g. by hydrolysis) to a NRIs, SRIs, NRI/SRIs, and adrenergic$_{\alpha 2}$ receptor antagonists. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5,113-191 (1991), Bundgaard, et al., *Journal of Drug Deliver Reviews,* 1992, 8:1-38, Bundgaard, *J. of Pharmaceutical Sciences,* 1988, 77:285 et seq.; and Higuchi and Stella (eds.) *Prodrugs as Novel Drug Delivery Systems,* American Chemical Society (1975).

Within the present invention, NRIs, SRIs, NRI/SRIs, and adrenergic$_{\alpha 2}$ receptor antagonists may be prepared in the form of pharmaceutically acceptable salts, including salts of organic acids and minerals. The acid addition salts of NRIs are preferred.

Further, the compounds of the present invention may exist in unsolvated as well as in solvated forms with pharmaceutically acceptable solvents such as water, ethanol, and the like. In general, the solvated forms are considered equivalent to the unsolvated forms for the purpose of the present invention.

A pharmaceutical composition for use in accordance with the present invention comprises a norepinephrine reuptake inhibitor, or a serotonin reuptake inhibitor and norepinephrine reuptake inhibitor, or a pharmaceutically acceptable salt thereof, together with a pharmaceutically acceptable carrier. The composition may comprise one or more norepinephrine reuptake inhibitor(s), or one or more each of serotonin reuptake inhibitor(s) and norepinephrine reuptake inhibitor(s) as active ingredient(s), together with one or more pharmaceutically acceptable carrier(s).

A pharmaceutical composition for use in accordance with the present invention comprises a norepinephrine reuptake inhibitor, or an adrenergic$_\alpha$2 receptor antagonist and norepinephrine reuptake inhibitor, or a pharmaceutically acceptable salt thereof, together with a pharmaceutically acceptable carrier. The composition may comprise one or more norepinephrine reuptake inhibitor(s), or one or more each of adrenergic$_\alpha$2 receptor antagonist(s) and norepinephrine reuptake inhibitor(s) as active ingredient(s), together with one or more pharmaceutically acceptable carrier(s).

Some of the compounds of the present invention may contain chiral centers and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron,* 33:2725 (1977); Eliel, E. L. *Stereochemistry of Carbon Compounds,* (McGraw-Hill, N.Y., 1962); Wilen, S. H. *Tables of Resolving Agents and Optical Resolutions,* p. 268 (E. L. Eliel, Ed., University of Notre Dame Press, Notre Dame, Ind. 1972).

A pharmaceutical for use in accordance with the present invention comprises NRI alone, NRI/SRI or NRI in combination with at least one adrenergic$_{\alpha 2}$ receptor antagonist, or a pharmaceutically acceptable salt thereof, together with a pharmaceutically acceptable carrier. The composition may comprise one or more NRI(s), one or more each of NRI and SRI, one or more of NRI/SRI(s) or one or more of each of NRI and adrenergic$_{\alpha 2}$ receptor antagonist as active ingredient(s), together with one or more pharmaceutically acceptable carrier(s).

The term "combination therapy" refers to the administration of two or more therapeutic agents or compounds to treat a therapeutic condition or disorder described in the present disclosure, for example hot flush, sweating, thermoregulatory-related condition or disorder, or other. Such administration includes co-administration of these therapeutic agents or compounds in a simultaneous manner, such as in a single compound having NRI/adrenergic$_{\alpha 2}$ receptor antagonist activity or in multiple, separate compounds for each NRI, SRI or adrenergic$_{\alpha 2}$ receptor antagonist activities. In addition, such administration also includes use of each type of therapeutic agent in a concurrent manner. In either case, the treatment regimen will provide beneficial effects of the drug combination in treating the conditions or disorders described herein.

The route of administration may be any route, which effectively transports the active norepinephrine reuptake inhibitor(s) or serotonin reuptake inhibitor(s) and norepinephrine reuptake inhibitor(s) to the appropriate or desired site of action, such as oral, nasal, pulmonary, transdermal, such as passive or iontophoretic delivery, or parenteral, e.g. rectal, depot, subcutaneous, intravenous, intraurethral, intramuscular, intranasal, ophthalmic solution or an ointment. Furthermore, the administration of norepinephrine reuptake inhibitor(s) and serotonin reuptake inhibitor(s) may be concurrent or simultaneous.

The term "subject" or "patient" refers to an animal including the human species that is treatable with the compositions, and/or methods of the present invention. The term "subject" or "subjects" is intended to refer to both the male and female gender unless one gender is specifically indicated. Accordingly, the term "patient" comprises any mammal which may benefit from treatment or prevention of vasomotor disturbances, such as a human, especially if the mammal is female, either in the pre-menopausal, peri-menopausal, or post-menopausal period. Furthermore, the term patient comprises female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause and the term "post-menopausal" means after the menopause. "Ovariectomy" means removal of an ovary or ovaries and can be effected according to Merchenthaler et al., *Maturitas*, 1998, 30(3): 307-316.

"Side effect" refers to a consequence other than the one(s) for which an agent or measure is used, as the adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and flushes (Janowsky, et al., *Journal of Clinical Psychiatry*, 1984, 45(10 Pt 2): 3-9).

EXAMPLES

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

General Methods

Reagents: Venlafaxine and O-Desmethyl-venlafaxine (DVS-233 or ODV) may be prepared as described in U.S. Pat. No. 4,535,186. Desipramine can be prepared as described in U.S. Pat. No. 3,454,554. Reboxetine can be prepared as described in U.S. Patent Publication No. 2002/0107249. 1-[1-(3-chlorophenyl)-2-(4-methyl-1-piperazinyl) ethyl]cyclohexanol(racemic), R-1-[1-(3-chlorophenyl)-2-(4-methyl-1-piperazinyl)ethyl]cyclohexanol, S-1-[1-(3-chlorophenyl)-2-(4-methyl-1-piperazinyl)ethyl] cyclohexanol, 1-[1-(3-chlorophenyl)-2-(dimethylamino) ethyl]cyclohexanol, 1-[1-(3-chloro-phenyl)-2-piperazin-1-yl-ethyl]-cyclohexanol and 1-[2-(dimethylamino)-1-(3-trifluoromethylphenyl)ethyl]cyclohexanol may be prepared as described in U.S. Pat. No. 4,826,844 (piperazine derivatives) or U.S. Pat. No. 4,535,186 (dimethylamino derivatives). The following reagents were purchased commercially: fluoxetine (Sigma, St. Louis, Mo.), morphine alkaloid pellets (Murty Pharmaceuticals, Lexington, Ky.), atipamezole (Pfizer, N.Y., N.Y.), ketamine (Phoenix Pharmaceuticals, Belmont, Calif.), and naloxone (Research Biochemicals International, St. Louis, Mo.).

Dosinq: All doses were prepared based on mg/kg. Compounds were dissolved in sterile water, 0.25% Tween/methylcellulose or 2.0% Tween/methylcellulose and injected subcutaneously (sc) or intraperitoneally (ip), and used at the following dosages: venlafaxine (1, 8, 10, 20, and 40 mg/kg), ODV (1, 10, 30 and 60 mg/kg), fluoxetine (10, 20, 60 mg/kg), desipramine (0.01, 1.0, 10, and 30 mg/kg), reboxetine (0.01, 1.0, 10, 30 and 60 mg/kg), R-1-[1-(3-chlorophenyl)-2-(4-methyl-1-piperazinyl)ethyl]cyclohexanol (30 mg/kg, ip), R-1-[1-(3-chlorophenyl)-2-(4-methyl-1-piperazinyl)ethyl]cyclohexanol, (30 mg/kg, ip), S-1-[1-(3-chlorophenyl)-2-(4-methyl-1-piperazinyl)ethyl]cyclohexanol, (30 mg/kg, ip), 1-[1-(3-chloro-phenyl)-2-piperazin-1-yl-ethyl]-cyclohexanol (30 mg/kg, ip), 1-[1-(3-chlorophenyl)-2-(dimethylamino)ethyl]cyclohexanol (30 mg/kg, sc), 1-[2-(dimethylamino)-1-(3-trifluoromethylphenyl)ethyl] cyclohexanol (30 mg/kg, sc), and atipamezole (1 mg/kg). Ketamine (Ketaject, Phoenix Pharmaceuticals, Belmont, Calif.) was injected intramuscularly in the hind limb at a dosage (40 mg/kg) that was determined to be mildly sedative but did not cause a change in tail skin temperature.

Animals: Ovariectomized Sprague-Dawley rats (180-220 g) were obtained from a commercial vendor (Taconic, Germantown, N.Y.) and individually housed under 12 hours light/dark cycle in a room maintained at 25° C. Animals were provided with standard rat chow and water ad libitum.

Morphine-dependent model: Ovariectomized rats were injected once daily for 8-9 days with vehicle to minimize stress responses and then administered compound(s) on test day. On day 4 of dosing, morphine dependence was induced by sc implantation of two slow-release morphine pellets (75 mg/pellet) in the dorsal scapular region. This model is based upon an established morphine-dependent naloxone-induced flush paradigm that is reversible by estrogen treatment (Katovich et al., *Proceedings of the Society for Experimental Biology & Medicine,* 1990, 193(2): 129-35). Four to six days after implantation, morphine withdrawal was induced with an opioid antagonist (naloxone) that causes a transient increase in TST. In a typical experiment, rats were administered their final dose of test compound 40 to 60 minutes prior to naloxone injection. Rats were mildly sedated with ketamine and a thermistor connected to a MacLab data acquisition system was taped to the base of the tail. Tail skin temperature was then monitored continuously for 35 minutes to establish a baseline temperature. Naloxone was subsequently administered and TST was measured for an additional 35 to 60 minutes (total recording time 70 to 95 minutes).

Telemetry model: This model has been modified from a previously reported protocol describing estrogen regulation of diurnal TST patterns (Berendsen et al., 2001). Over a 24-hour period, intact cycling rats decrease TST during the active (dark) phase and TST remains elevated during the inactive (light) phase. In OVX rats, TST is elevated over the entire 24-hour period, thus the usual decrease in TST during the active (dark) phase is lost, thus, a compound's ability to restore this lowering of TST during the active phase was examined. A temperature and physical activity transmitter (PhysioTel TA10TA-F40, Data Sciences International) was implanted subcutaneously in the dorsal scapular region and the tip of the temperature probe was tunneled subcutaneously 2.5 cm beyond the base of the tail. After a 7-day recovery period, TST readings were continuously recorded for the remainder of the study. Tail skin temperature readings were collected from each animal every 5 minutes with values obtained over a 10 second sampling period. The day before test day, an average baseline TST value was calculated for each animal by averaging temperature readings recorded during the 12 hours active (dark) phase. In these studies, animals were dosed approximately 1 hour prior to the onset of dark cycle.

Statistical analysis: To analyze changes in TST induced by naloxone in morphine-dependent rats, all data were analyzed using a two factor repeated measure ANOVA for "treatment" and "time." The model was fit to test whether there were significant differences in the responses between treatment groups. Naloxone administration is designated as time zero and data is then analyzed at 5 minute intervals. The first three readings were averaged and used as baseline TST scores. All data were analyzed as ΔTST (TST for each time point—baseline). Multiple comparisons (LSD p-values) among the treatment groups at each time point were used for the analysis. Efficacy of hot flush abatement was determined by evaluating statistical differences at the peak response time of 15 minutes post-naloxone, when the maximal change in TST is observed. A customized SAS-excel (SAS Institute, Cary, N.C.) application was used applying a four parameter logistic model to determine $ED_{50}$ values. A logistic dose transformation was performed on ΔTST. Maximum flush (ΔTST at 15 minutes post-naloxone) was used in the analysis and the minimum was locked at zero. The $ED_{50}$ value is reported as the dose of test compound that abates 50% of the naloxone—induced flush. Statisticians in the Biometrics Department (Wyeth Research, Collegeville, Pa.) developed a customized JMP application.

Evaluation of a compound's ability to restore normal lowering of TST in the telemetry model was analyzed using hourly TST values calculated for each animal by averaging the 12 temperature readings obtained every 5 minutes over that recording time. To analyze ΔTST in the telemetry model, a two factors repeated measure ANOVA was performed. The model used for analysis was ΔTST=GRP (group)+HR (hours)+GRP*HR+BASELINE. Thus, the reported least squares means are the expected mean values as if both groups had the same baseline value. Post-hoc tests of hourly GRP*HR samples are t-tests of the difference between groups for each hour. To be conservative, a result was not considered significant unless the p-value was <0.025. All analyses were performed using SAS PROC MIXED (SAS, Carey, N.C.).

Example 1

Figure 3:
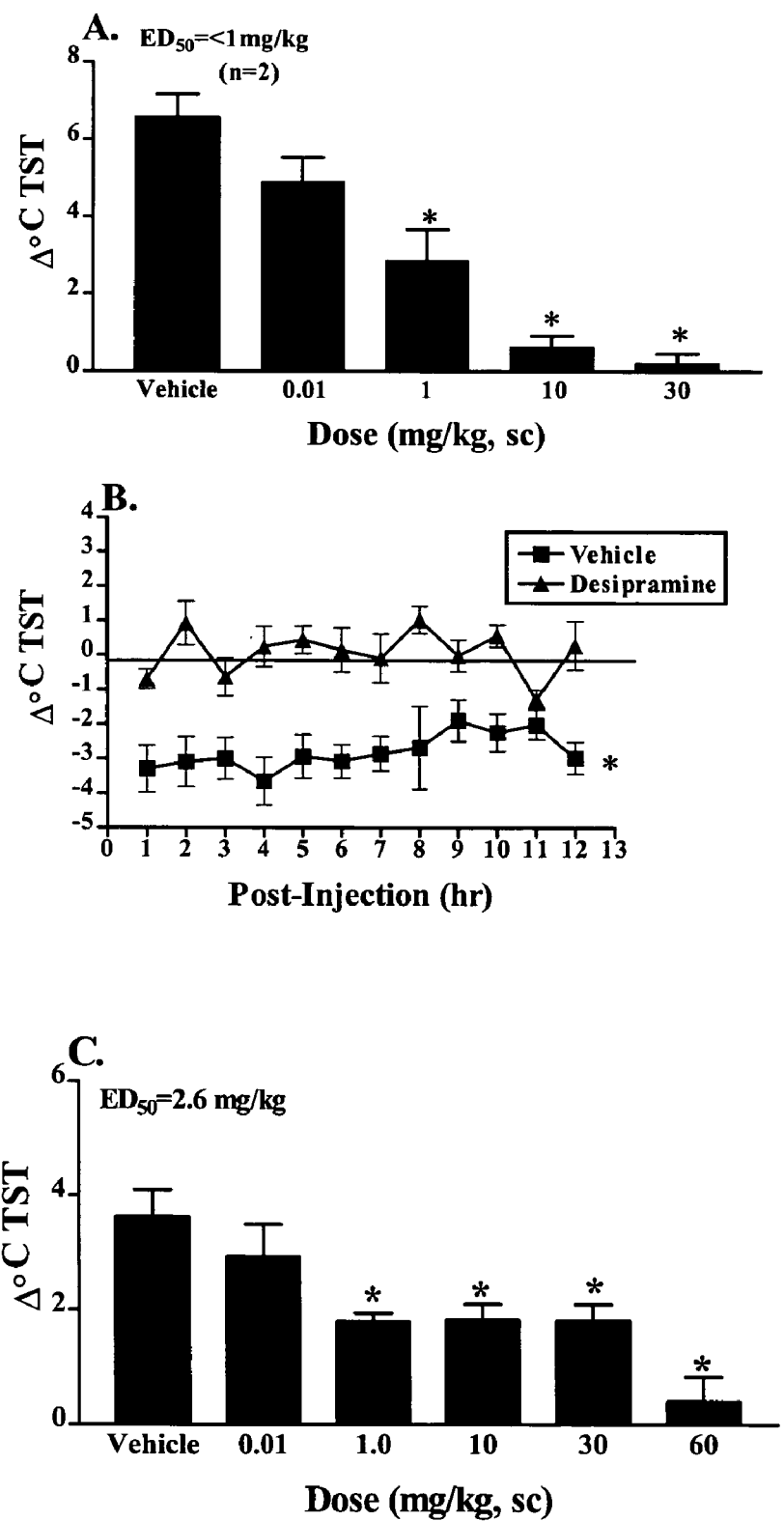
FIGS. 3A through 3F are graphical representations of the effect of NRIs in alleviating vasomotor instabilities, as exemplified in Example 1.

Effect of NRIs in Alleviating Vasomotor Instability in Pre-Clinical Models of Vasomotor Instability Method used as described in the general method section under morphine-dependent rat model with the following exceptions: Rats were injected subcutaneously with vehicle (sterile $H_2O$) or desipramine that may be prepared as described in U.S. Patent Publication No. 2002/0107249, dissolved in sterile $H_2O$ and administered at 0.1, 1.0, 10 and 30 mg/kg 1 hour prior to naloxone (FIG. 3A). At maximal flush (15 minutes post-naloxone; Δ° C., Mean+SEM) desipramine dose-dependently abates the naloxone-induced flush.

Rats were injected subcutaneously with vehicle (sterile $H_2O$) or desipramine dissolved in sterile $H_2O$ and administered at 10 mg/kg (FIG. 3B). Changes in TST (Δ° C., Mean+SEM) over time in the telemetry model of OVX-induced thermodysregulation demonstrate that desipramine significantly decreases TST over the entire length of the active phase (FIG. 3B). An analysis of results indicated that desipramine at doses of 10 mg/kg and 30 mg/kg was able to abate 90.4% and 96.7%, respectively, of naloxone-induced hot flush in a rat model of vasomotor instability. In addition, NRI compounds can be used to restore normal thermoregulation as depicted in the OVX-induced thermoregulatory dysfunction telemetry model.

Method used as described in the general method section under morphine-dependent rat model with the following exceptions: Rats were injected subcutaneously with vehicle (sterile $H_2O$) or reboxetine that may be prepared as described in U.S. Pat. No. 4,229,449, dissolved in sterile $H_2O$ and administered at 0.01, 1.0, 10, 30 and 60 mg/kg) 1 hour prior to naloxone (FIG. 3C). At maximal flush (15 minutes post-naloxone; Δ° C., Mean+SEM) reboxetine dose-dependently abates the naloxone-induced flush.

Method as described in the general method section under morphine-dependent rat model with the following exceptions: Rats were injected subcutaneously with vehicle (sterile $H_2O$), reboxetine (which was prepared as described in U.S. Patent Publication No. 2002/0107249 A1, dissolved in sterile $H_2O$ and administered at 0.01, 1.0, 10, 30, 60 mg/kg) or 1-[1-(3-chlorophenyl)-2-(4-methyl-1-piperazinyl)ethyl]cyclohexanol (which was prepared as described in U.S. Pat. No. 4,826,844, dissolved in sterile $H_2O$ and administered at 7.5, 15, 30 mg/kg). Changes in TST (Δ° C., Mean) over time in the morphine-dependent rat model depict that both reboxetine (FIG. 3D) and 1-[1-(3-chlorophenyl)-2-(4-methyl-1-piperazinyl)ethyl]cyclohexanol (FIG. 3E) dose-dependently abate the naloxone-induced flush. These results indicate that increasing NE levels with NRIs can alleviate vasomotor instability.

Method used as described in the general method section under morphine-dependent rat model with the following exceptions: Rats were injected intraperitoneally with vehicle (0.25% Tween/methylcellulose) or 1-[1-(3-chlorophenyl)-2-(dimethylamino)ethyl]cyclohexanol (WY-781), and 1-[2-(dimethylamino)-1-(3-trifluoromethylphenyl)ethyl]cyclohexanol (WY-867), prepared in accordance with U.S. Pat. No. 4,535,186, dissolved in 0.25% Tween/methylcellulose and administered at 30 mg/kg) 1 hour prior to naloxone (FIG. 3F). At maximal flush (15 minutes post-naloxone; $\Delta°$ C., Mean+SEM) both compounds abated the naloxone-induced flush in the MD model.

Example 2

Effect of a Combination of NRI and SRI on Alleviation of Vasomotor Instability

Method are described in the general method section under morphine-dependent rat model with the following exceptions: Rats were injected subcutaneously with vehicle sterile $H_2O$), desipramine, (which was prepared as described in U.S. Pat. No. 3,454,554, dissolved in sterile $H_2O$ and administered at 0.1, 1.0, 10 mg/kg) or fluoxetine (Sigma, dissolved in sterile $H_2O$ at 10, 30, 60 mg/kg) or combination of fluoxetine administered at 10 mg/kg and increasing doses of desipramine listed above 1 hour prior to naloxone.

At maximal hot flush (15 minutes post-naloxone; $\Delta°$ C., Mean+SEM) desipramine dose-dependently abates the naloxone-induced flush in the MD model but results in a shallow slope of the estimated line (solid line, FIG. 4). The shallow slope of the estimated line is typical of compounds that have multiple site interactions. Therefore, a dose of fluoxetine that did not abate the naloxone-induced flush was used to determine if there was an interaction between the NE and 5-HT systems. In the presence of 10 mg/kg fluoxetine, the slope of the estimated line for the desipramine dose response curve shifted to a natural sigmoidal curve indicative of a single site action. These data indicate that in the presence of saturating concentrations of fluoxetine, desipramine is acting solely through the NE system. Although the $ED_{50}$ value for desipramine (1 mg/kg) did not change in the presence of fluoxetine, the maximally effective dose was shifted to the left. The results indicated that an NRI compound (desipramine, 10 mg/kg) abated a naloxone-induced hot flush and was significantly enhanced when the serotonin reuptake inhibitor (SRI), fluoxetine (10 mg/kg) was co-administered. Hence, the co-administration of a NRI and SRI compound (e.g. desipramine+fluoxetine) was more efficacious for treating hot flush.

Example 3

Figure 5:
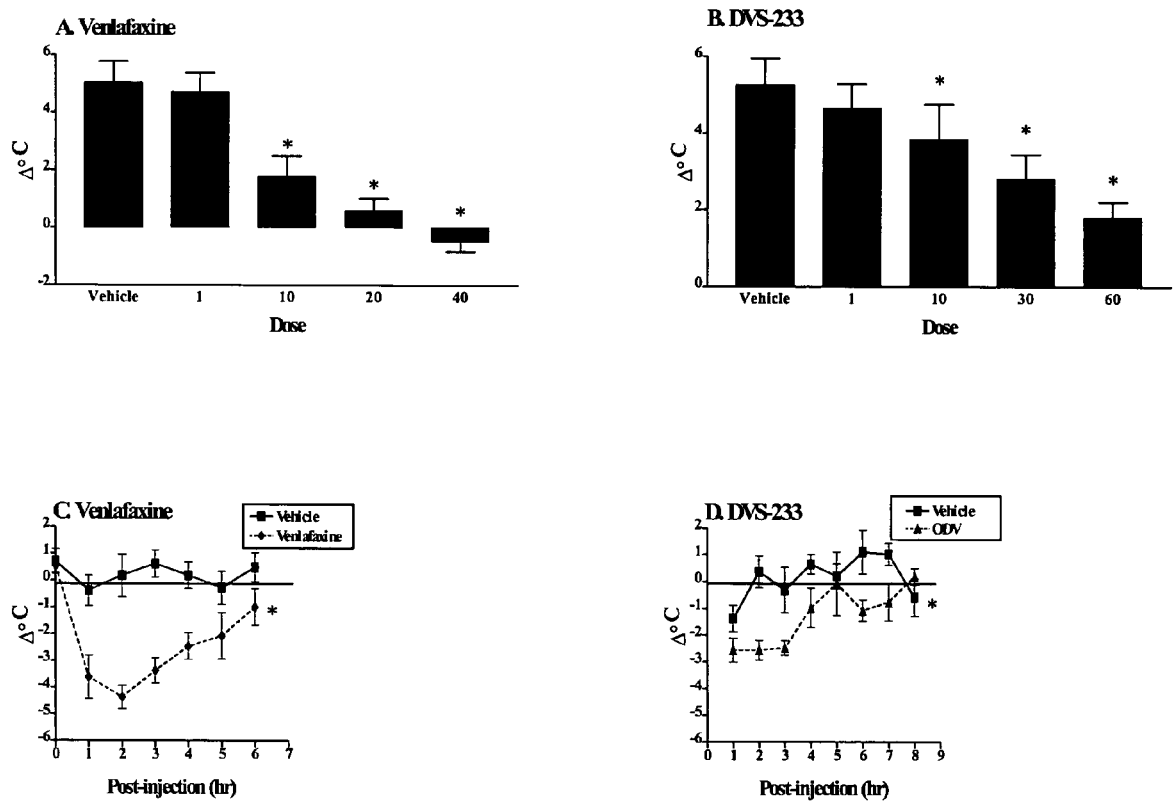
FIGS. 5A, 5B, 5E, 5F, 5G, 5H and 5J show dose response of venlafaxine, DVS-233/ODV, R-venlafaxine, S-venlafaxine, R-ODV, S-ODV, and paroxetine in MD model, respectively.
FIGS. 5C and 5D show venlafaxine (15 mg/kg, sc) and DVS-233 (60 mg/kg, sc) in a telemetry model (* indicates p<0.05 compared to vehicle control) (referred to in Example 3).

Effect of Compounds with Dual NRI/SRI Activity on Alleviating Vasomotor Instability Method as described in the general method section under morphine-dependent rat model with the following exceptions: Rats were injected subcutaneously with vehicle (sterile $H_2O$), venlafaxine (dissolved in sterile $H_2O$ and administered at 1.0, 10, 20, 40 mg/kg) or, DVS-233 (dissolved in sterile $H_2O$ and administered at 1.0, 10, 30, 60 mg/kg) 1 hour prior to naloxone. Venlafaxine and DVS-233 were synthesized as described in U.S. Pat. No. 4,535,186. At maximal flush (15 minutes post-naloxone; $\Delta°$ C., Mean+SEM) venlafaxine dose-dependently ($ED_{50}$ value=15+7 mg/kg) abates the naloxone-induced flush (FIG. 5A). At maximal flush (15 minutes post-naloxone; $\Delta°$ C., Mean+SEM) DVS-233 dose-dependently $ED_{50}$ value=30+3 mg/kg) abates the naloxone-induced flush (FIG. 5B).

Method of FIGS. 5C and 5D were as described in the general method section under telemetry model. Rats were injected subcutaneously with vehicle (sterile $H_2O$), venlafaxine (dissolved in sterile $H_2O$ and administered at 15 mg/kg) or DVS-233 (dissolved in sterile $H_2O$ and administered at 60 mg/kg). Changes in TST ($\Delta°$ C., Mean+SEM) over time in the telemetry model demonstrated that venlafaxine significantly and transiently decreased TST during the active phase (FIG. 5C). Changes in TST ($\Delta°$ C., Mean+SEM) over time in the telemetry model of demonstrated that DVS-233 significantly and transiently decreases TST during the active phase (FIG. 5D). The results indicated that venlafaxine and DVS-233, dual acting SRI/NRI, effectively alleviated vasomotor instability. The results indicated that dual acting compounds alleviate vasomotor instability by modulating the NE system via the NRI component.

Method as described in the general method section under morphine-dependent rat model with the following exceptions: Rats were injected subcutaneously with vehicle (sterile $H_2O$), R-enantiomer of venlafaxine (R-venlafaxine, which was synthesized as described in U.S. Pat. No. 4,535,186, dissolved in sterile $H_2O$ and administered at 0.3, 1.0, 10, 30 mg/kg), S-enantiomer of venlafaxine (S-venlafaxine, which was synthesized as described in U.S. Pat. No. 4,535,186, dissolved in sterile $H_2O$ and administered at 1.0, 10, 30, 60 mg/kg), R-enantiomer of O-desmethylvenlafaxine (R-ODV, which was synthesized as described in U.S. Pat. No. 4,535,186, dissolved in sterile $H_2O$ and administered at 1.0, 10, 30, 60 mg/kg), S-enantiomer of ODV (S-ODV, which was synthesized as described in U.S. Pat. No. 4,535,186, dissolved in sterile $H_2O$ and administered at 1.0, 10, 30, 60 mg/kg), or paroxetine (which was synthesized as described in U.S. Pat. No. 4,535,186, dissolved in sterile $H_2O$ and administered at 0.5, 5.0, 15, 30 mg/kg) 1 hour prior to naloxone administration. At maximal flush (15 minutes post-naloxone; $\Delta°$ C., Mean+SEM), R-venlafaxine dose-dependently ($ED_{50}$ value=8.3+3 mg/kg) abates the naloxone-induced flush (FIG. 5E). At maximal flush (15 min post-naloxone; $\Delta°$ C., Mean+SEM) S-venlafaxine dose-dependently ($ED_{50}$ value=10.9+3 mg/kg) abates the naloxone-induced flush (FIG. 5F). At maximal flush (15 minutes post-naloxone; $\Delta°$ C., Mean+SEM) R-ODV dose-dependently ($ED_{50}$ value=14.4+13 mg/kg) abates the naloxone-induced flush (FIG. 5G). At maximal flush (15 minutes post-naloxone; $\Delta°$ C., Mean+SEM) S-ODV dose-dependently ($ED_{50}$ value=13.3+8 mg/kg) abates the naloxone-induced flush (FIG. 5H). At maximal flush (15 minutes post-naloxone; $\Delta°$ C., Mean+SEM) paroxetine dose-dependently ($ED_{50}$ value=22.3+11 mg/kg) abates the naloxone-induced flush (FIG. 5J). The doses used for R-venlafaxine, S-venlafaxine, R-ODV, S-ODV and paroxetine were chosen based on their activity on the NE system or NE transporter system. The results indicate that R-venlafaxine, S-venlafaxine, R-ODV, S-ODV and paroxetine that all have dual SRI/NRI activity effectively alleviate hot flush. The results indicate that compounds with dual activity alleviate vasomotor instability by increasing the NE/5-HT balance and therefore NE transmission.

Example 4

Effect of Desipramine on Adrenergic$_{\alpha2}$ Antagonist-induced Vasomotor Instability Method as described in the general method section with the following exceptions: Rats were injected subcutaneously with vehicle (sterile H$_2$O), atipamezole HCl (selective adrenergic$_{\alpha2}$ receptor antagonist) (Pfizer, N.Y., N.Y., dissolved in sterile H$_2$O administered at 0.3 mg/kg), desipramine (dissolved in sterile H$_2$O and administered at 1 mg/kg) or with a combination of atipamezole and desipramine. Atipamezole was administered 55 minutes prior to naloxone injection and desipramine was administered 40 minutes prior to naloxone (FIG. 6).

Figure 6:
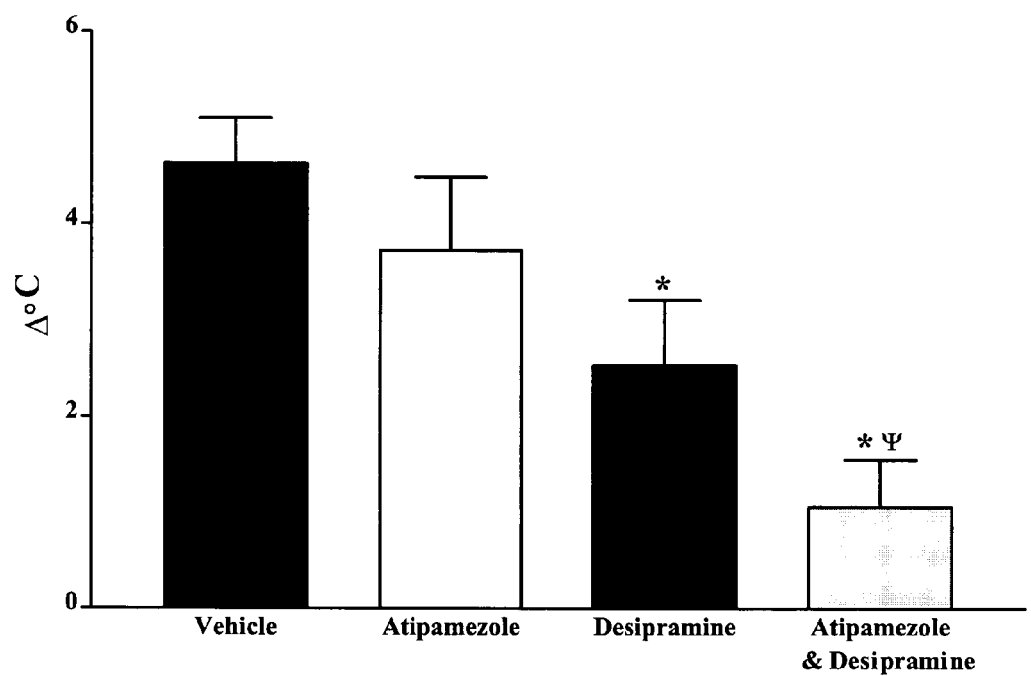
FIG. 6 demonstrates an additive effect of an $\alpha_2$-adrenergic antagonist (atipamezole) in combination with desipramine on a naloxone-induced flush in the MD model (referred to in Exampl 4).

Changes in TST (Δ° C., Mean) after naloxone administration demonstrated that atipamezole alone was not significantly different from vehicle treated rats (FIG. 6). Desipramine alone abated the naloxone-induced flush by approximately 50% whereas, in combination with atipamezole, an additive effect was noted. The additive effect noted with the combination of atipamezole and desipramine, infer that the adrenergic$_{\alpha2}$ receptor is involved in vasomotor instability. Furthermore, these data indicated that the efficacy of desipramine was enhanced when administered in combination with an adrenergic$_{\alpha2}$ receptor antagonist.

Example 5

Functional uptake activity for the Human Mono amin Uptake Transporters

Cell Lines and Culture Reagents

MDCK-Net6 cells, stably transfected with human hNET, as described in Pacholczyk, T., R. D. Blakely, and S. G. Amara, *Nature*, 1991, 350(6316): 350-4, were cultured in growth medium containing high glucose DMEM (Gibco, Cat. No. 11995), 10% FBS (dialyzed, heat-inactivated, US Bio-Technologies, Lot FBD1129HI) and 500 μg/ml G418 (Gibco, Cat. No. 10131). Cells were plated at 300,000/T75 flask and cells were split twice weekly. The JAR cell line (human placental choriocarcinoma) was purchased from ATCC (Cat. No. HTB-144). The cells were cultured in growth medium containing RPMI 1640 (Gibco, Cat. No. 72400), 10% FBS (Irvine, Cat. No. 3000), 1% sodium pyruvate (Gibco, Cat. No. 1136) and 0.25% glucose. Cells were plated at 250,000 cells/T75 flask and split twice weekly. For all assays, cells were plated in Wallac 96-well sterile plates (PerkinElmer, Cat. No. 3983498).

Norepinephrine (NE) Uptake Assay

On day 1, cells were plated at 3,000 cells/well in growth medium and maintained in a cell incubator (37° C., 5% CO2). On day 2, growth medium was replaced with 200 μl of assay buffer (25 mM HEPES; 120 mM NaCl; 5 mM KCl; 2.5 mM CaCl2; 1.2 mM MgSO$_4$; 2 mg/ml glucose (pH 7.4, 37° C.)) containing 0.2 mg/ml ascorbic acid and 10 μM pargyline. Plates containing cells with 200 μl of assay buffer were equilibrated for 10 minutes at 37° C. prior to addition of compounds. A stock solution of desipramine was prepared in DMSO (10 mM) and delivered to triplicate wells containing cells for a final test concentration of 1 μM. Data from these wells were used to define non-specific NE uptake (minimum NE uptake). Test compounds were prepared in DMSO (10 mM) and diluted in assay buffer according to test range (1 to 10,000 nM). Twenty-five microliters of assay buffer (maximum NE uptake) or test compound were added directly to triplicate wells containing cells in 200 μl of assay buffer. The cells in assay buffer with test compounds were incubated for 20 minutes at 37° C. To initiate the NE uptake, [3H]NE diluted in assay buffer (120 nM final assay concentration) was delivered in 25 μl aliquots to each well and the plates were incubated for 5 minutes (37° C.). The reaction was terminated by decanting the supernatant from the plate. The plates containing cells were washed twice with 200 μl assay buffer (37° C.) to remove free radioligand. The plates were then inverted, left to dry for 2 minutes, then reinverted and air dried for an additional 10 minutes. The cells were lysed in 25 μl of 0.25 N NaOH solution (4° C.), placed on a shake table and vigorously shaken for 5 minutes. After cell lysis, 75 μl of scintillation cocktail was added to each well and the plates were sealed with film tape. The plates were returned to the shake table and vigorously shaken for a minimum of 10 minutes to ensure adequate partitioning of organic and aqueous solutions. The plates were counted in a Wallac Microbeta counter (PerkinElmer) to collect the raw cpm data.

Serotonin (5-HT) Uptake Assay

The methods for 5-HT functional reuptake using the JAR cell line were modified using a previous literature report. Prasad, P. D., et al., *Placenta*, 1996, 17(4): 201-7. On day 1, cells were plated at 15,000 cells/well in 96-well plates containing growth medium (RPMI 1640 with 10% FBS) and maintained in a cell incubator (37° C., 5% CO2). On day 2, cells were stimulated with staurosporine (40 nM) to increase the expression of the 5-HT transporter. On day 3, cells were removed from the cell incubator two hours prior to assay and maintained at room temperature to equilibrate the growth medium to ambient oxygen concentration. Subsequently, the growth medium was replaced with 200 μl of assay buffer (25 mM HEPES; 120 mM NaCl; 5 mM KCl; 2.5 mM CaCl2; 1.2 mM MgSO4; 2 mg/ml glucose (pH 7.4, 37° C.)) containing 0.2 mg/ml ascorbic acid and 10 μM pargyline. A stock solution of paroxetine (AHR-4389-1) was prepared in DMSO (10 mM) and delivered to triplicate wells containing cells for a final test concentration of 1 μM. Data from these wells were used to define non-specific 5-HT uptake (minimum 5-HT uptake). Test compounds were prepared in DMSO (10 mM) and diluted in assay buffer according to test range (1 to 1,000 nM). Twenty-five microliters of assay buffer (maximum 5-HT uptake) or test compound were added directly to triplicate wells containing cells in 200 μl of assay buffer. The cells were incubated with the compound for 10 minutes (37° C.). To initiate the reaction, [3H] hydroxytryptamine creatinine sulfate diluted in assay buffer was delivered in 25 μl aliquots to each well for a final test concentration of 15 nM. The cells were incubated with the reaction mixture for 5 minutes at 37° C. The 5-HT uptake reaction was terminated by decanting the assay buffer. The cells were washed twice with 200 μl assay buffer (37° C.) to remove free radioligand. The plates were inverted and left to dry for 2 minutes, then reinverted and air-dried for an additional 10 minutes. Subsequently, the cells were lysed in 25 μl of 0.25 N NaOH (4° C.) then placed on a shaker table and shaken vigorously for 5 minutes. After cell lysis, 75 μl of scintillation cocktail was added to the wells, the plates were sealed with film tape and replaced on the shake table for a minimum of 10 minutes. The plates were counted in a Wallac Microbeta counter (PerkinElmer) to collect the raw cpm data.

Evaluation of Results

For each experiment, a data stream of cpm values collected from the Wallac Microbeta counter was downloaded to a Microsoft Excel statistical application program. Determination of percent specific NE uptake (% SB) at 1 μM are calculated using a Microsoft Excel spread sheet applying the following formula: [% SB of NE reuptake (% SB)=[(1−(mean cpm control wells—each cpm drug well)/(mean cpm control wells—mean cpm non-specific wells))×100]. Calculations of $EC_{50}$ values were made using the transformed-both-sides logistic dose response program written by Wyeth Biometrics Department. The statistical program uses mean cpm values from wells representing maximum binding or uptake (assay buffer) and mean cpm values from wells representing minimum binding or uptake ((1 µM desipramine (hNET) or 1 µM paroxetine (hSERT)). Estimation of the $EC_{50}$ value was completed on a log scale and the line was fit between the maximum and minimum binding or uptake values. All graphic data representation was generated by normalizing each data point to a mean percent based on the maximum and minimum binding or uptake values. The $EC_{50}$ values reported from multiple experiments were calculated by pooling the raw data from each experiment and analyzing the pooled data as one experiment. The results are shown in Table 1.

TABLE 1

Functional uptake activity for the Human Monoamine Uptake Transporters

| Compound | hNET $EC_{50}$ (nM) | hSERT $EC_{50}$ (nM) |
|---|---|---|
| desipramine | 3.0 | 392 |
| nisoxetine | 7.0 | 275 |
| 1-[1-(3-fluorophenyl)-2-(4-methyl-1-piperazinyl)ethyl]cyclohexanol (prepared in accordance with Example 25 of US-A-4,826,844) | 240 | Inactive at 1 µM |
| 1-[1-(3-chlorophenyl)-2-(4-methyl-1-piperazinyl)ethyl]cyclohexanol (prepared in accordance with Example 26 of US-A-4,826,844) | 55 | 15,500 |
| 1-[2-(4-methyl-1-piperazinyl)-1-[3-(trifluoromethyl)-phenyl]ethyl]cyclohexanol (prepared in accordance with Example 27 of US-A-4,826,844) | 87 | 33,580 |

| | % Specific NE uptake | % Specific NE uptake |
|---|---|---|
| 1-[1-(4-methoxyphenyl)-2-[4-methyl-1-piperazinyl)ethyl]cyclohexanol (prepared in accordance with Example 28 of US-A-4,826,844) | 65 | 79 |
| 1-[1-(3-chlorophenyl)-2-[4-(3-chlorophenyl)-1-piperazinyl]ethyl]cyclohexanol (prepared in accordance with Example 19 of US-A-4,826,844) | 23 | 72 |
| 1-[1-(3-methoxyphenyl)-2-[4-phenylmethyl)-1-piperazinyl]ethyl]cyclohexanol (prepared in accordance with Example 15 of US-A-4,826,844) | 43 | 49 |
| 1-[2-(3-chlorophenyl)1-piperazinyl]-1-[3-methoxyphenyl)ethyl]cyclohexanol (prepared in accordance with Example 18 of US-A-4,826,844) | 64 | 67 |
| 1-[2-[4-(6-chloro-2-pyrazinyl)-1-piperazinyl]-1-[3-methoxyphenyl)ethyl]cyclohexanol (prepared in accordance with Example 23 of US-A-4,826,844) | 59 | 58 |
| 1-[2-[4-(phenylmethyl)]-1-piperazinyl]-1-[3-(trifluoromethyl)phenyl]ethyl]cyclohexanol (prepared in accordance with Example 16 of US-A-4,826,844) | 19 | 94 |
| 1-[1-(3-methoxyphenyl)-2-[4-[3-(trifluoromethyl)-phenyl]-1-piperazinyl]ethyl]cyclohexanol (prepared in accordance with Example 20 of US-A-4,826,844) | 38 | 87 |
| 1-[1-(4-fluorophenyl)-2-[4-(phenylmethyl)-1-piperazinyl]ethyl]cyclohexanol (prepared in accordance with Example 17 of US-A-4,826,844) | 53 | 88 |
| 1-[1-(3-methoxyphenyl)-2-[4-[3-(trifluoromethyl)-phenyl]-1-piperazinyl]ethyl]cyclopentanol (prepared in accordance with Example 21 of US-A-4,826,844) | 57 | 82 |

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method for treating vasomotor symptoms caused by thermoregulatory dysfunction selected from the group consisting of hot flushes, excessive perspiration, night sweats, and combinations thereof in a subject in need thereof, comprising the step of:
    administering to said subject a therapeutically effective amount of milnacipran or pharmaceutically acceptable salt thereof,
    wherein said amount is less than about 37.5 mg/day.
2. A method according to claim 1,
    wherein said amount is less than about 30 mg/day.
3. A method according to claim 1,
    wherein said amount is less than about 25 mg/day.
4. A method according to claim 1,
    wherein said amount is less than about 20 mg/day.
5. A method according to claim 1,
    wherein said amount is less than about 15 mg/day.
6. A method according to claim 1,
    wherein said amount is less than about 10 mg/day.
7. A method according to claim 1,
    wherein said amount is less than about 5 mg/day.
8. A method according to claim 1,
    wherein said vasomotor symptom is hot flush.
9. A method according to claim 1,
    wherein said subject is human.
10. A method according to claim 9,
    wherein said human is a female.
11. A method according to claim 10,
    wherein said female is pre-menopausal.
12. A method according to claim 10,
    wherein said female is peri-menopausal.
13. A method according to claim 10,
    wherein said female is post-menopausal.
14. A method according to claim 9,
    wherein said human is a male.
15. A method according to claim 13,
    wherein said male is naturally, chemically or surgically andropausal.

* * * * *